United States Patent [19]

Silvus, Jr. et al.

[11] Patent Number: 5,486,768
[45] Date of Patent: Jan. 23, 1996

[54] SURFACE RESISTIVITY METER FOR DETERMINING SURFACE DEGRADATION OF HIGH RESISTIVITY MATERIALS

[75] Inventors: Howard S. Silvus, Jr., San Antonio; William A. Mallow, Helotes; Charles H. Parr; Jerome J. Dziuk, both of San Antonio, all of Tex.

[73] Assignee: Southwest Research Institute, San Antonio, Tex.

[21] Appl. No.: 251,393

[22] Filed: May 31, 1994

[51] Int. Cl.⁶ .................................................. G01R 27/02
[52] U.S. Cl. .......................... 324/718; 324/715; 324/724; 324/688
[58] Field of Search ....................................... 324/688, 724, 324/718, 715, 700

[56] References Cited

U.S. PATENT DOCUMENTS 2,811,691  1/1954  Dahm et al. .
3,048,776  6/1959  Logan .
3,147,430  2/1962  Greenler .
4,446,424  5/1984  Chatanier ................................ 324/709
4,546,310  10/1985  Chatanier ................................ 324/709
4,724,376  2/1988  Slough et al. .
4,758,777  7/1988  Bossard et al. .
4,962,360  10/1990  Homma et al. .
5,093,626  3/1992  Baer ........................................ 324/709

Primary Examiner—Maura K. Regan
Assistant Examiner—Jose M. Solis
Attorney, Agent, or Firm—Baker & Botts

[57] ABSTRACT

Apparatus and method for determining the amount of oxidative and hydrolytic degradation in the surface of a highly resistive material, such as a polymer. A special probe provides an annular resistance on the surface of a sample of the material. The voltage drop across the sample determines the input to a meter circuit. A guard circuit has an applied voltage that is substantially the same as the voltage at the meter circuit input. This circuitry permits a very low voltage source to be used.

12 Claims, 4 Drawing Sheets

SURFACE RESISTIVITY METER FOR DETERMINING SURFACE DEGRADATION OF HIGH RESISTIVITY MATERIALS

The U.S. Government has a paid-up license in this invention and the rights in limited circumstances to require the patent owner to license others on reasonable terms as provided for by the terms of Contract No. DAAK70-85-C-0007 awarded by the U.S. Army Belvoir Research, Development and Engineering Center.

TECHNICAL FIELD OF THE INVENTION

This invention relates in general to the field of electronic instrumentation. More particularly, the present invention relates to a meter for determining the surface oxidative and hydrolytic degradation of materials having initially a high electrical surface resistivity, which is altered proportionate to the degradation.

BACKGROUND OF THE INVENTION

Fabric-reinforced elastomeric tanks are often used for storing fuel or other liquids. These tanks may be required to hold fuel for extended periods of time while exposed to harsh environmental conditions, but then may be folded and stored for years before being used again.

The tanks may deteriorate as a result of being stored in warehouses having extreme climates. Heat and humidity are harmful to the elastomers commonly used for the tanks. As polymers undergo environmental aging, the surface chemistry is the initial area of breakdown and change, which includes oxidative and hydrolytic attack. This alters the surface free energy. The surface resistivity drops incrementally and in proportion to the degree of oxidative and hydrolytic attack. Also, although the tanks are drained after use, residual fuel usually remains in them, which can degrade the polymer over time. For handling ease and to save warehouse space, the tanks may be tightly folded and packed into crates. The stress concentrations caused by the folds can lead to premature failure of the tanks.

Accordingly, a need has arisen for a method of determining the condition of polymeric fuel tanks so that unreliable tanks can be taken out of service. A change in surface resistivity of the polymeric portion of a tank could mean a tank is unfit for service. However, the surface resistance of a polymer material is typically very high, and conventional low-voltage ohmmeters are not sufficiently sensitive. Conventional high-voltage ohmmeters usually apply a potential on the order of several hundred volts across the specimen. However, when measuring the surface resistance of fuel tanks, there is a high probability that flammable fuel vapors will be present in the area. In this environment, an electrical potential of large magnitude could produce a spark of sufficient energy to cause fuel-vapor ignition. Furthermore, there is an electrical shock hazard to personnel.

SUMMARY OF THE INVENTION

The resistivity meter of the present invention is especially suited for field testing of polymeric fuel tanks equipment. It can be used to measure differences in electrical conductivity on the surface of polymeric materials in different phases of degradation. This measurement can be used to determine if a tank is fit for service. The method is fast and reliable. Its probe design requires no special surface preparation other than cleaning.

An advantage of the invention is that it provides a low voltage ohmmeter for surface resistivity measurements of highly resistive materials. For these high resistance measurements, stray shunt resistances are nulled, thereby minimizing error. From these measurements, the extent to which the material is degraded can be determined. The ohmmeter is safe as well as effective, and is easy to use. For testing, a simple direct contact of the material with a probe is sufficient. A quick-charge feature speeds the measurement process.

One aspect of the invention is an ohmmeter for measuring the value of an unknown surface resistance of a sample of material. A voltage source circuit applies a low voltage to the sample. A meter circuit, connected across the voltage source, provides an output signal that indicates the surface resistivity. The input circuit of the meter provides a high input impedance to the meter circuit at a measurement input node. A resistance circuit, connected between the input node and the voltage source, provides a reference resistance. A probe circuit, connected between the input node and circuit ground, has two electrodes for contacting the surface of the material. The probe circuit divides the voltage across the voltage supply circuit to provide a voltage at the input node that is monotonically related to the unknown resistance. A guard circuit, in electrical connection with the output of the meter circuit, shields connections to the input node. The combined gain of the input circuit and the meter circuit is approximately unity, so that the guard circuit is held at approximately the same voltage as the input node.

DETAILED DESCRIPTION OF THE INVENTION

The following description is directed to the use of a surface resistivity meter to determine whether polymeric fuel tanks are fit for service. As discussed above in the Background section of this patent application, this type of fuel tank presents a particular problem in that conventional resistivity meters are either ineffective or dangerous. The meter of the present invention is both effective and safe for this application. It is also useful for surface resistivity measurements in many other applications, especially where the material under test has high surface resistivity.

Figure 1:
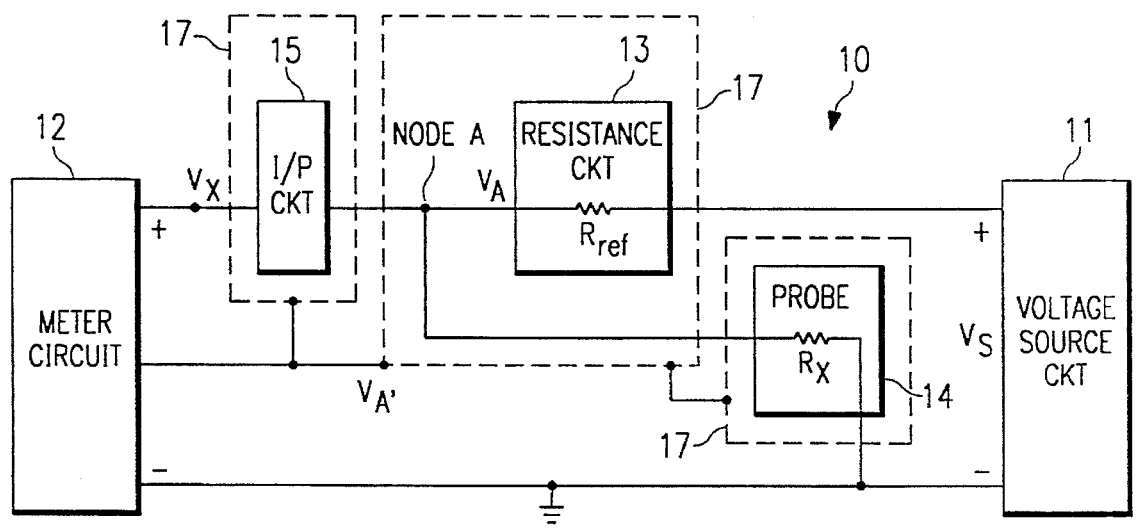
FIG. 1 is a block diagram of the basic components of the electrical circuitry of a surface resistivity meter in accordance with the invention.

FIG. 1 is a block diagram of a low voltage surface resistivity meter 10 in accordance with the invention. The general operating principle of meter 10 is that of a voltage divider. A voltage source 11 is connected to a meter circuit 12 through a resistor circuit 13 of known resistance and a high-impedance input circuit 15. A probe circuit 14 is placed across the unknown resistance of the material being measured and is connected in parallel with the meter circuit 12 and its high-impedance input circuit 15.

The voltage divider relation may be expressed as follows:

$$\frac{V_A}{V_s} = \frac{R_x}{R_x + R_{ref}},$$

where $V_s$ represents the applied voltage from source 11, $V_A$ represents the voltage at the input circuit 15, $R_x$ is the unknown surface resistance, and $R_{ref}$ is the known resistance of resistance circuit 13. The above equation may be solved for the unknown resistance, $R_x$.

As an overview of meter 10, voltage source 11 provides a supply voltage, in the order of 5 volts. Resistor circuit 13 provides the known resistance, $R_{ref}$. Probe 14 is a special probe designed to contact the surface of the material being measured with circular electrodes that define the area of the surface for which a resistivity measurement is desired. The face of the probe 14 defines an annular resistor, $R_x$, on the surface of the sample being measured. The voltage at the output of probe 14 is the input to input circuit 15, which is designed to prevent loading of the circuit by meter circuit 12. The input node, A, to input circuit 15 is the high-resistance node of the circuit, i.e., the node between resistors of the voltage divider. Meter circuit 12 is driven by input circuit 15 and actuates an indicator that can be calibrated to a scale on the face of meter 10 to provide a reading of the unknown resistance in ohms.

A feature of the invention is a "guard circuit" 17, which minimizes the effects of electrical leakage across various insulators within the internal circuitry of meter 10 and probe 14. To implement this guarding, various conductive elements of resistor circuit 13, probe 14, and input circuit 15 are shielded. Essentially, the shielded elements are those in electrical connection to node A, which is the measurement input node to input circuit 15. The shielding is comprised of coaxial cables, housings, or the like, which have conductive outer layers. A voltage, $V_{A'}$, is applied to these conductive layers of guard circuit 17. This voltage, $V_A$, is provided by meter circuit 12, and it is the electrical connections among the shielding layers to this output that form guard circuit 17. The combined gain of input circuit 15 and meter circuit 12 is unity, so that $V_{A'}$ is substantially the same as $V_A$. Guard circuit 17 is further explained below in connection with FIGS. 5 and 6.

Figure 2:
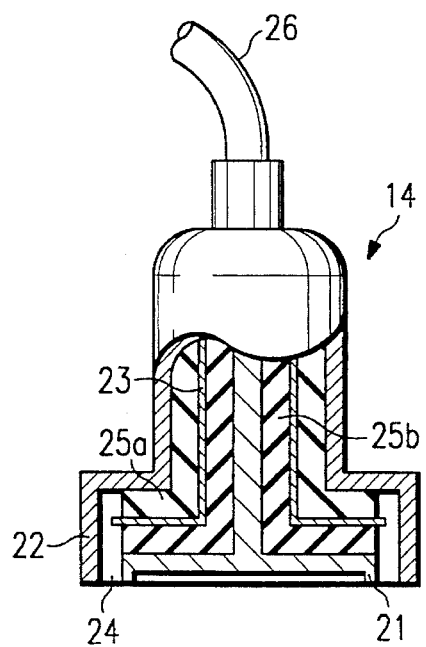
FIG. 2 is a cross sectional view of a probe for contacting the sample to be measured.
Figure 3:
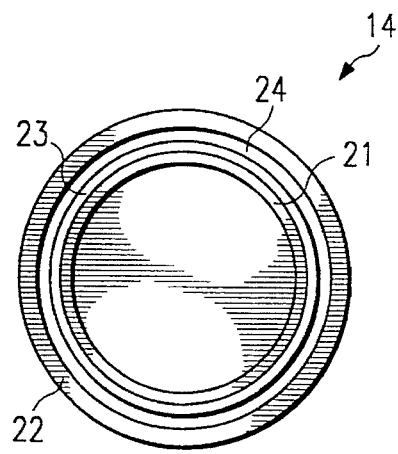
FIG. 3 is a bottom plan view of the probe of FIG. 2.

FIGS. 2 and 3 illustrate probe 14 in further detail. FIG. 2 is a cross sectional side view of probe 14 and FIG. 3 is a bottom plan view. Inner and outer electrodes 21 and 22 are made from conductive material and contact the surface of the material whose surface resistivity is being measured.

Electrode 21 is ring-shaped at its bottom surface, so as to contact an annular surface area of the material. Electrode 21 may be a conductive disk, whose inner area is recessed so as to require less force for a good contact around its edges. The annular resistance between the outside diameter of electrode 21 and the inside diameter of electrode 22 is the unknown resistance, Rx, of FIG. 1. Electrode 22 is ring shaped, concentric to but spaced from electrode 21. The difference between the inside diameter of electrode 22 and the outside diameter of electrode 21 is small relative to the thickness of the sample so that surface effects are maximized.

At the bottom surface of probe 14, electrodes 21 and 22 are spaced apart by an air gap 24. Inside probe 14, electrodes 21 and 22 are separated by two insulating layers 25a and 25b.

Electrodes 21 and 22 are connected to the rest of the circuit by means of a triaxial cable 26. As shown in FIG. 1, electrode 21 is connected to node A, supplying the input voltage Va. Electrode 22 is connected to ground.

A third electrode 23 is embedded between insulating layers 25a and 25b, such that it forms a third conductive ring between electrodes 21 and 22. At the bottom surface of probe 14, electrode 23 extends into air gap 24, but does not touch the surface of the material being measured. Nor does electrode 23 touch electrodes 21 or 22. This third electrode 23 is referred to herein as "guard electrode" 23 for reasons explained below in connection with FIGS. 5 and 6. Essentially, electrode 23 is held at guard voltage, $V_{A'}$, which is equal to the input voltage, $V_A$, from electrode 21. Because electrodes 21 and 23 are at the same electrical potential, no leakage current can flow between electrodes 21 and 23 and, hence, no leakage current can flow between electrodes 21 and 22.

The contacting surface of electrode 21 is large in relation to the width of air gap 24. As a result, when electrode 21 is on contact with a material being measured, the near-surface resistivity of the material contributes principally to the measured resistance, Rx. Resistance of an annular resistor may be expressed as:

$$R = \left[ \sigma \cdot \ln \frac{D_O}{D_I} \right] / 2\pi, \quad (1)$$

where $R$ = Resistance of annular surface resistor;
$\sigma$ = Surface resistivity of the material;
$D_O$ = Outside diameter of annulus; and
$D_I$ = Inside diameter of annulus.

Figure 4:
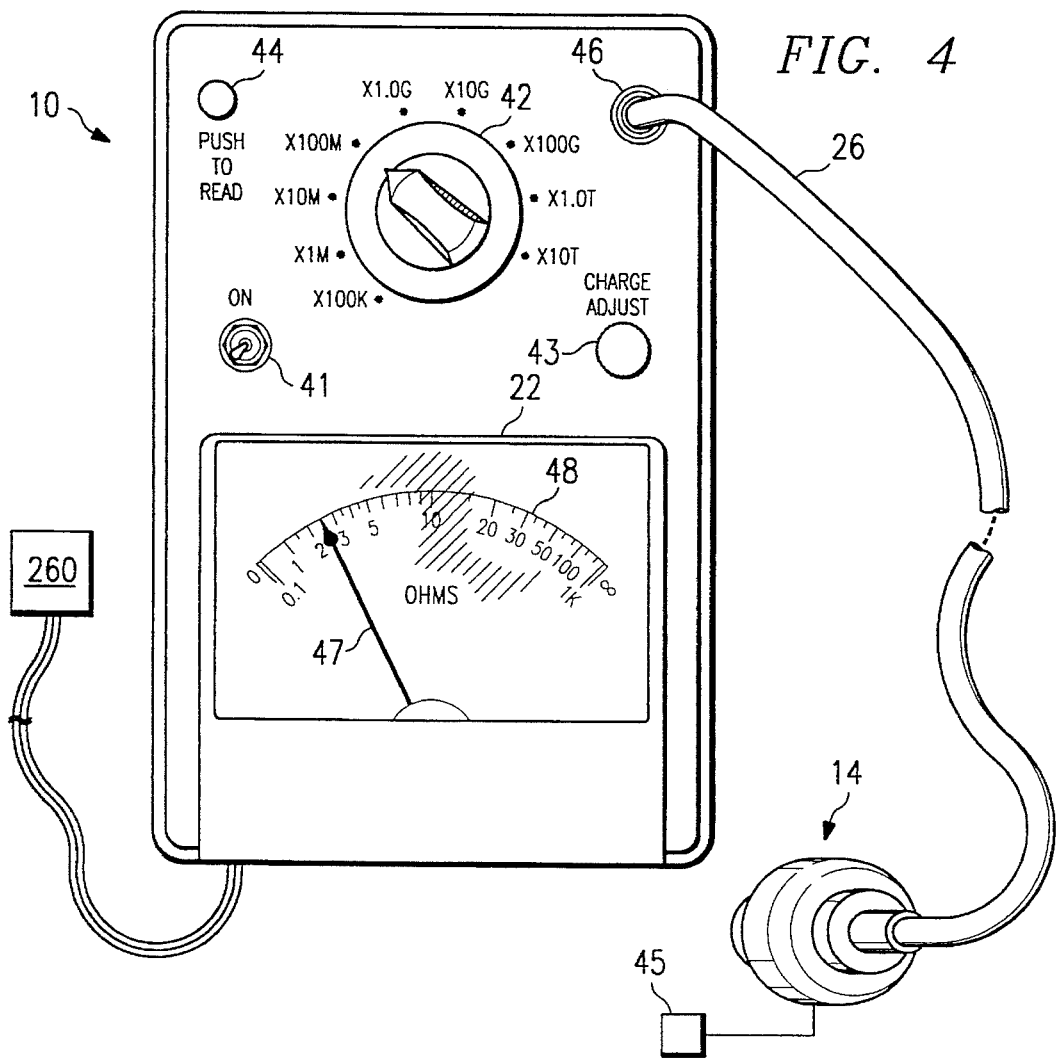
FIG. 4 illustrates the front face of a housing for the meter.

FIG. 4 illustrates the face of meter 10, which is housed in a casing, sized for portability. Meter 10 includes various user-operated input devices, namely on/off switch 41, range select dial 42, charge adjust knob 43, and push-to-read button 44. The operational aspects of these selection devices are explained below in connection with FIGS. 5 and 6. Needle indicator 47 is actuated by a signal representing the measured resistance, Rx, and moves over a measurement scale 48. As shown, the measurements obtained by meter 10 will be surface resistivity in units of ohms.

Figure 5:
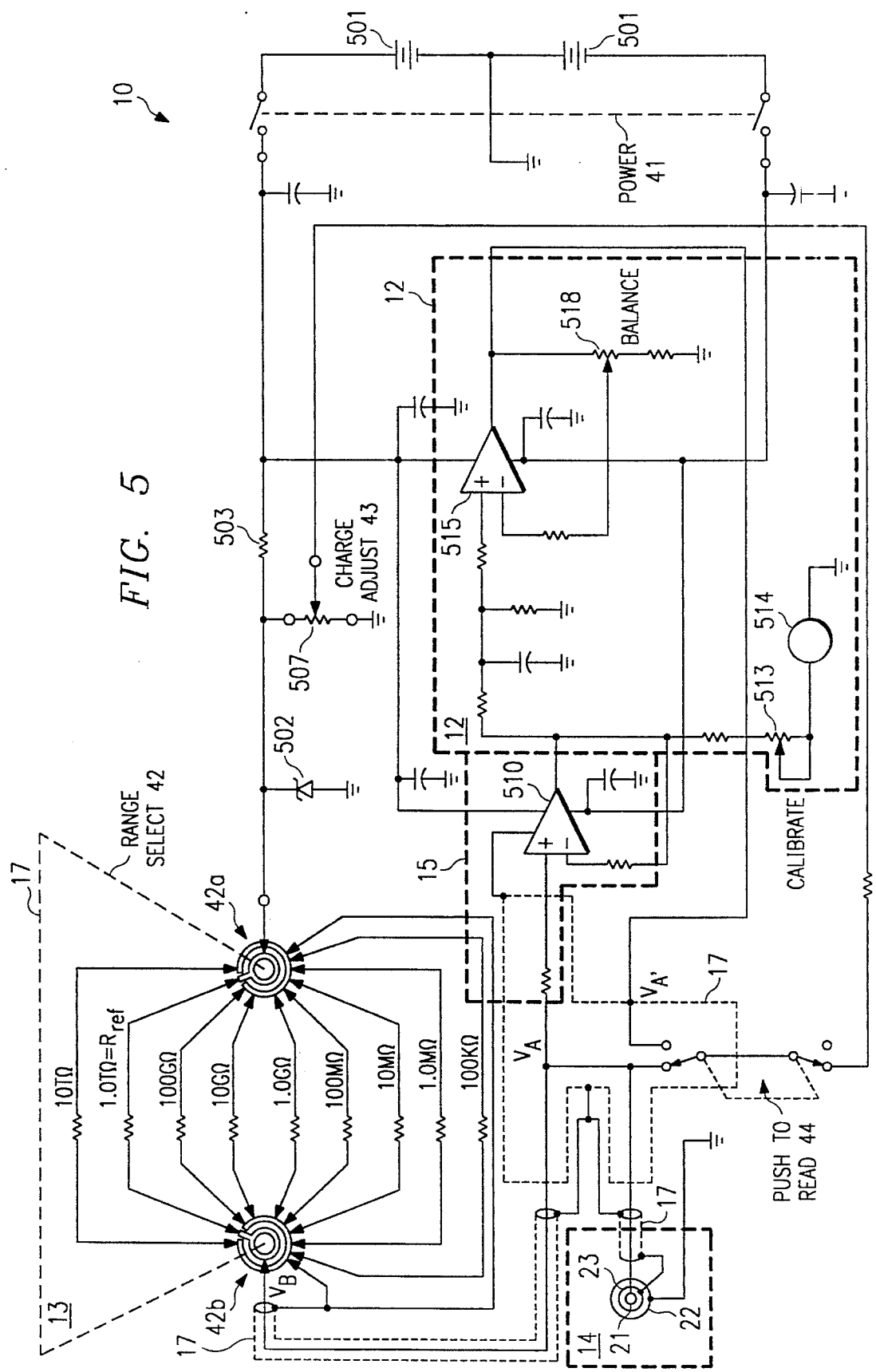
FIGS. 5 and 6 are schematic diagrams of the circuit of FIG. 1.

FIG. 5 is a schematic diagram of the meter 10 of FIG. 1. The various circuits are indicated with heavy dashed lines. Other components that implement the various input devices of FIG. 4 are also shown. FIG. 5 also illustrates the two nodes, A and A', of FIG. 1, whose voltages, $V_A$ and $V_{A'}$, are substantially equal because of the unity gain of input circuit 15 and meter circuit 12.

Supply circuit is comprised primarily of batteries 501, which are switched into and out of the circuit by switch 41. Batteries 501 may be conventional 9 volt alkaline batteries connected in series with a center tap connection to ground, thereby yielding supply voltages of +9 and −9 volts. Positive and negative voltages pass through the poles of switch 41 before connection to the rest of the circuit. A zener diode 502 functions as a voltage regulator and maintains a circuit reference voltage of approximately five volts. Resistor 503 is a current limiter. A number of capacitors perform bypass functions to prevent high frequency oscillations.

Diode 502 is connected to a charge adjust potentiometer 507. The "arm" of potentiometer 507 is mechanically connected to charge adjust knob 43. The operation of potentiometer 507 is explained below in connection with a "quick-charge" feature of the invention.

Diode 502 is also connected to terminal pole 42a of range select dial 42, which selects one of a number of reference resistors that comprise resistance circuit 13. The selected reference resistor, $R_{ref}$ is connected between terminals 42a and 42b. In the example of this description, select dial 42 is positioned such that $R_{ref}$=1.0 Tohms. Other reference resistors have values ranging from 10 Tohms to 100 Kohms. Values for reference resistors are chosen in accordance with the requirements of specific applications.

The other terminal 42b of select dial 42 is connected to measuring electrode 21 of probe 14, as well as to the measurement input node, A. A terminal of push-to-read button 44 is also connected to node A.

As indicated by the dotted lines, various electrical connections to node A are surrounded by a cable shield, which has an insulating layer and a conductive outer layer. The conductive outer layer of all shielding is electrically connected to guard electrode 23, as well as to the output of meter circuit 12. The unselected range resistors and the housing of push-to-read button 44 are also shielded, with the shielding being in electrical connection with the output of meter Circuit 12. These shieldings and their connection to each other and to node A' comprise guard circuit 17.

Input circuit 15 is comprised of an operational amplifier 510. The non-inverting input to operational amplifier 510 is connected to node A via an oscillation suppressing resistor. The inverting input is connected to the output via a feedback resistor. The high input impedance of input circuit 15 permits input currents at low levels of 60 fA or less.

The output of operational amplifier 510 is connected to a series combination of a resistor, calibration potentiometer 513, and an actuator 514 for needle 47. Calibration potentiometer 513 is used to adjust the full-scale deflection of needle actuator 514. Meter 10 may be calibrated so that needle indicator 47 has full-scale deflection when the source voltage, Vs, is applied to its input terminals. Then, the deflection of needle 47 is linearly proportional to $V_A/Vs$. During measurements, the unknown resistance Rx is non-linearly related to $V_A/VS$. The value of the selected resistor $R_{ref}$ and the function related to deflection do not interact. This permits scale 48 to be calibrated in resistance units that are independent of the actual decade range being used, with the decade multiplier set by select dial 42. At half deflection, where $V_A/VS=0.5$, the values of Rx and Rs are equal. In other embodiments, the analog output of operational amplifier 510 could be converted to a digital signal for digital readings.

The output of operational amplifier 510 is also connected to the non-inverting input of a second operational amplifier 515. This connection is via a combination of resistors and a capacitor, which attenuate interference and suppress oscillations. The inverting input of operational amplifier 515 is connected to a feedback path from its output.

The output of operational amplifier 515 is connected to the conductive shielding of guard circuit 17. Operational amplifier 515 has a low output impedance for driving guard circuit 17. It is also connected to a balance potentiometer 518, which is in a feedback path to the inverting input. By tuning balance potentiometer 518, the voltage, $V_{A'}$, at the output of operational amplifier 515 can be adjusted so that the combination of input circuit 15 and meter circuit 12 has a unity gain.

A feature of meter 10 is its ability to keep stray shunt resistances higher than the resistance being measured. This is accomplished by the high input impedance of input circuit 15 and also by guard circuit 17. Because $V_{A'}$ is substantially equal to $V_A$, there is no potential difference between the shielded components and the surrounding guard conductors. Thus, there will be no current flow between them, which minimizes the effect of internal leakage currents from node A. Also, any leakage currents from external sources are diverted into guard circuit 17 and will flow to circuit ground.

Another feature of meter 10 is a quick-charge capability that minimizes the time required to achieve a stable reading from scale 48. As stated above, potentiometer 507 is connected across voltage source circuit 11. The arm of potentiometer 507 is connected to push-to-read button 44. Push-to-read button 44 is implemented as a double pole, double throw switch. When push-to-read button 44 is in its default position, it connects the arm of charge adjust potentiometer 507 to the non-inverting input of operational amplifier 510. In this default position, the voltage at the input of input circuit 15 comes from voltage supply circuit 11 as dropped by charge adjust potentiometer 507. Circuit capacitances quickly charge to this voltage. When activated (pushed), push-to-read button 44 disconnects charge adjust potentiometer 507 from node $V_A$. During this push to read state, the voltage level, $V_A$, at the non-inverting input of operational amplifier 510 is determined by resistance circuit 13 and the unknown resistance, Rx. If $V_A$ is equal to the voltage to which the circuit was charged, then the voltage remains constant and the reading of needle 47 does not change. However, if $V_A$ is different from the voltage to which the circuit was charged, then the output of meter circuit 12 drifts up or down causing the reading of needle 47 to change. The rate of drift depends on the time constant of the reference resistor and stray circuit capacitances. Furthermore, when button 44 is activated, its shielding is connected to guard circuit 17.

Figure 6:
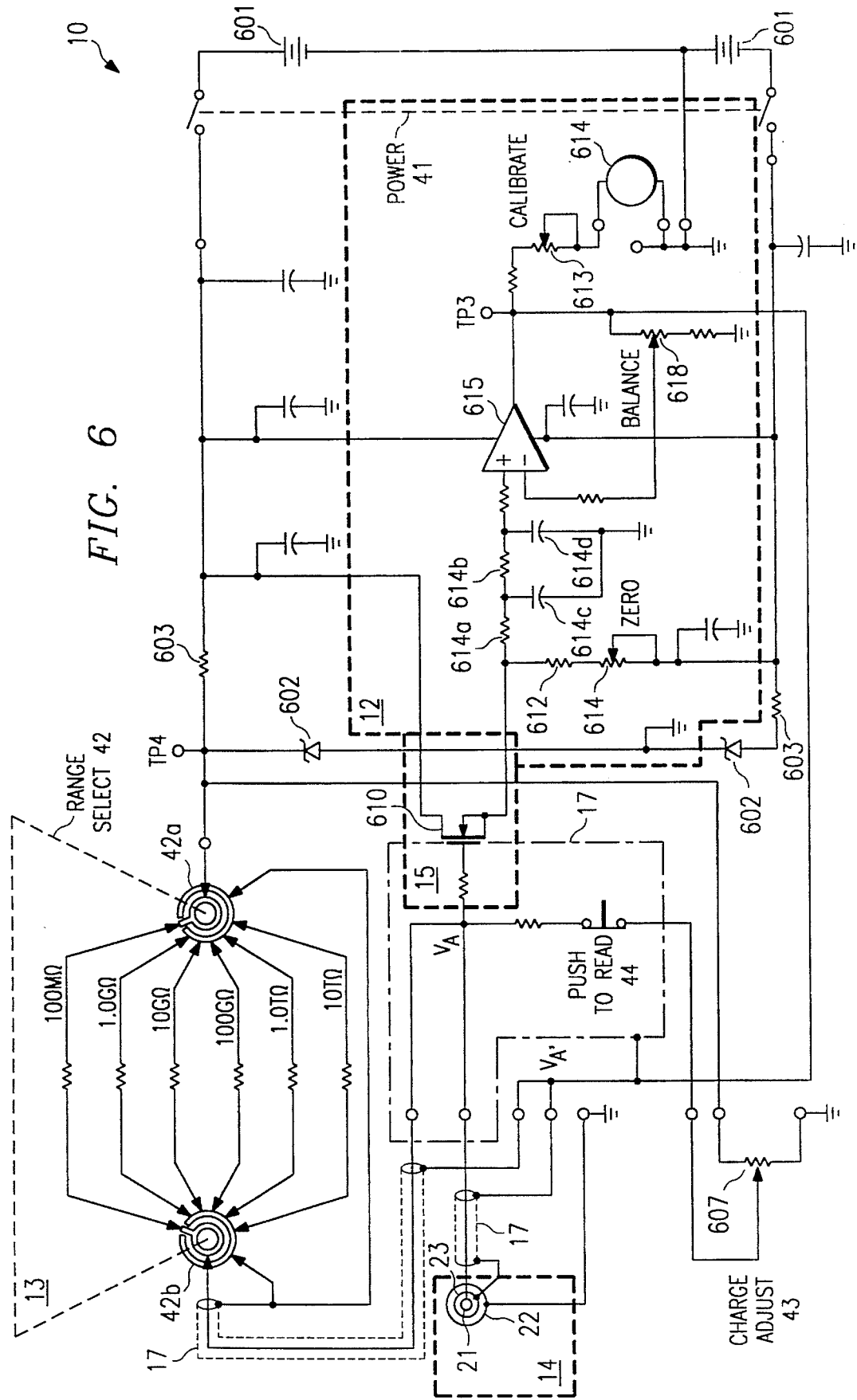

FIG. 6 illustrates an alternative schematic for meter 10. One difference is that input circuit 15 is comprised of a field effect transistor (MOSFET) 610 instead of an operational amplifier. The calibration potentiometer 613 and actuator 614 are connected to the output of a second operational amplifier 615.

The voltage source circuit of FIG. 6 is similar to that of FIG. 5. Power is supplied by batteries 601. Two zener diodes 602 and two current limiting resistors 603 provide positive and negative 5 volt supplies. The positive supply voltage is delivered to a supply terminal of charge adjust potentiometer 607, as well as to one terminal 42a of range select dial 42.

The resistor circuit 13, probe circuit 14, and guard circuit 17 of FIG. 6 are also similar to those of FIG. 5. Guard circuit has a conductive layer that is connected to the output of a second operational amplifier 615 of meter circuit 12. Because the combined gain of input circuit 15 and meter circuit 12 is unity, the output, $V_{A'}$, is substantially the same as the input voltage $V_A$, to input circuit 15.

Node A is a connection node for push-to-read button 44, to which the arm of charge adjust potentiometer 607 is connected. Charging of circuit capacitances occurs while push-to-read button 44 is in its default (closed) position, because the voltage at the gate of MOSFET 610 is controlled by potentiometer 607. However, when push-to-read button 44 is pressed, the input voltage at the gate of MOSFET 610 is controlled by the values of the selected reference resistor in resistance circuit 13 and the unknown resistance Rx between electrodes 21 and 22 of probe 14.

MOSFET 610 receives the input voltage, $V_A$. MOSFET 610 functions as a source follower, for which the source resistance is the series combination of resistor 612 and potentiometer 614. Adjustment of this source resistance using potentiometer 614 facilitates setting the source of MOSFET 610 to zero volts relative to ground. The source output of MOSFET 610 is also connected to a combination of resistors and capacitors that comprise a low pass filter for attenuating interference.

An operational amplifier 615 has a non-inverting input that receives the filtered output from MOSFET 610. A resistor at the input to operational amplifier 615 functions as an oscillation suppressor.

The output of operational amplifier 615 is connected to a balance potentiometer 618. Balance potentiometer 618 forms a voltage divider in the feedback path to the inverting input of operational amplifier 615. Using potentiometer 618, the gain of operational amplifier 615 can be adjusted to compensate the less-than-unity gain of MOSFET 610 so that the net gain from the gate of MOSFET 610 to the output of operational amplifier 615 is substantially unity.

The output of operational amplifier 615 is also connected to calibration potentiometer 613. Calibration potentiometer 613 adjusts the input to needle actuator 614, and is used to calibrate needle 47 as discussed above in connection with FIG. 5.

An example of when surface resistivity measurements are useful is the case of elastomeric tanks that are used to store fuels or other liquids. These tanks are used to hold fuel for some duration and then emptied and stored before being needed again. Stress concentrations caused by the folds and other storage conditions can lead to weaknesses in the tank material. Polymer materials used for other applications may also undergo degradation due to causes such as sunlight, rain, ozone, and fuels.

Operation of meter 10 provides measurements of surface resistivity of samples of different degrees of degradation. The invention is especially useful for polymers. The surface resistivity of such materials is normally very high, in the order of 1000–10,000 megohms. These materials display a definite trend toward decreasing resistivity as they age or otherwise deteriorate. The deterioration is accompanied by formation of ionic species, which in turn, increase conductivity. The correlation between surface resistivity and deterioration may be experimentally obtained for a certain material, to provide benchmark values. A database (not shown) may be used to store the experimentally derived values, so that the extent of deterioration of new samples can be ascertained.

For fuel tank testing, the fuel tank surface is first cleaned with detergent or solvent. The instrument is designed for use by holding the meter case in one hand, with the other hand pressing the probe tip on the surface of the tank. Basically, the meter operates by sending a shielded nonleaking current of electricity to the probe tip. This current is conducted by the probe tip to the surface of the tank. The current travels along the surface of the tank, bridges the gap between the two electrodes of the probe, and is returned to the meter. The amount of current returned is related to the surface resistance of the polymeric material. With surface resistivity being a function of the overall condition of the polymer, then the surface resistivity measurement is an indication of any physical or chemical changes that the material may have undergone.

Different elastomers have different resistivities. Also, changes in resistivity due to degradation vary with different materials. Therefore, the operator determines which type of material is being tested. The operator refers to the proper reference data for that material when analyzing the measurements.

During testing, it is important to maximize surface contact between the probe tip and the surface being tested. Ideally, the surface is flat and hard or capable of being pressed against a flat and hard surface. In the case of testing of a polymeric tank filled with liquid, the surface of the electrodes could be made slightly convex.

Although not illustrated, a spring-operated device could be added to the probe head, to measure the force being applied to the probe tip. This would permit the operator to consistently apply the same force for each measurement, and thereby obtain reproducible readings.

In operation, meter 10 is intended to be used with its front panel lying in a horizontal plane. Meter 10 may be placed on a table or bench for laboratory work, or it may be hand-held for field use. The operating steps are listed below:

1. Set range select dial 42 to a desired resistance range.
2. Use charge adjust knob 43 to set the meter needle 47 at center scale or other desired position.
3. Place probe 14 firmly against the material to be tested so that the entire outer ring 22 of the probe face is in contact with the material.
4. While holding probe 14 in place, press push-to-read button 44.
5. Note the direction that the meter needle 47 moves.
6. Release push-to-read button 44 and use charge adjust knob 43 to relocate the meter needle 47 to a new setting in the direction of the drift observed in Step 5. For example, if the needle 47 was previously set to mid scale (10) and drift was observed to be downscale, it would be appropriate to set the needle 47 to a downscale value (e.g., 3). If drift is fairly fast, then needle 47 should be relocated a substantial distance from the original setting; on the other hand, if drift is very slow, the needle 47 should be moved only a short distance. Note that speed of drift is a function of the range setting. On the lowest range, drift rate for a given degree of error will be many times faster than on the highest range. If the observed drift was very fast, it may be necessary to change ranges.
7. With the new setting of charge adjust knob 43, again place probe 14 in firm contact with the same location on the sample, and press push-to-read button 44. Again, note the direction and speed of drift, if any. Repeat Step 6 until needle 47 does not drift or drifts very slowly when push-to-read button 44 is depressed. At this point, needle 47 holds a position indicating unknown resistance. When this condition is achieved, proceed to the next step.
8. Release push-to-read button 44 and read meter 10. Multiply the meter reading by the range setting to determine sample surface resistivity in ohms.

Additionally, for the embodiment of FIG. 6, the instrument adjustment procedure is as follows:

1. With the on/off button 41 in the OFF position and meter 10 resting on a table or bench with the front panel in a horizontal plane and facing upward, adjust a mechanical-zero screw (not shown) of the meter to set needle 47 at "0" on the scale.
2. Gain access to the circuit board.
3. Connect a short circuit between the measuring electrode 21 and ground electrode 22 of the probe 14.
4. Move the power switch 41 to the ON position.
5. Adjust zero potentiometer 614 to produce a zero reading on scale 48.
6. Remove the short circuit from the probe 14 and set select dial 42 to the lowest range.
7. Connect a floating (i.e., not connected to power-line ground) voltmeter (not shown) between test points TP3 and TP4 of the circuit. Set this floating voltmeter for 1 to 2 volts full scale, or whatever full-scale setting is available within this range.
8. Adjust balance potentiometer 618 to produce a reading of zero on the floating voltmeter.
9. Disconnect the floating voltmeter.
10. With dial 42 set to the lowest range and probe 14 lying on its side so that the measuring contact area of electrode 21 is exposed only to air, press push-to-read button 44 and adjust calibrate potentiometer 613 for a full-scale reading on scale 48.

11. Release push-to-read button 44 and rotate charge adjust dial 43 through its entire range. With dial 43 in a minimum position, the front-panel scale 48 should read zero "0". With dial 43 in a maximum position, scale 48 should read full scale (∞).

12. Move the charge adjust dial 43 to its maximum position and set the select dial 42 to the highest range. Depress push-to-read button 44 and note whether or not needle 47 drifts. If there is drift, make a very small adjustment of balance potentiometer 618 to counteract the drift. After adjustment is made, release the push-to-read button 44 and repeat this step until drift with push-to-read button 44 depressed is zero or very slow. If this step is properly done, full-scale calibration of the instrument will not be affected significantly. When fine adjustment of potentiometer 618 has been completed, return the instrument to its case and turn the power off.

Other Embodiments

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. An ohmmeter for measuring the value of an unknown surface resistance of a sample of material, comprising:

a voltage source circuit for supplying a low reference voltage;

a meter circuit connected across said unknown surface resistance for providing an output signal indicative of said unknown surface resistance;

an input circuit at the input to said meter circuit for providing a high input impedance to said meter circuit at a measurement input node;

a resistance circuit connected between said input node and said voltage source circuit, for receiving said reference voltage and for providing a reference resistance;

a probe circuit connected to said input node, said probe circuit having two electrodes for contacting the surface of said material, one connected to ground, thereby providing said unknown surface resistance, which divides the voltage across said voltage supply circuit to provide a voltage at said input node that is related to said unknown surface resistance;

a guard circuit for shielding connections to said input node, said guard circuit being in electrical communication with the output of said meter circuit;

wherein the combined gain of said input circuit and said meter circuit is adjustable to approximately unity; and a quick charge circuit having a quick charge switch connected across said resistance circuit for bypassing said resistance circuit during charging of circuit capacitances.

2. The ohmmeter of claim 1, wherein said voltage source circuit supplies a voltage less than 10 volts.

3. The ohmmeter of claim 1, wherein said input circuit is an operational amplifier.

4. The ohmmeter of claim 1, wherein said input circuit is a field effect transistor.

5. The ohmmeter of claim 1, wherein said quick charge circuit further comprises a charge potentiometer connected to said voltage source circuit for adjusting said reference voltage before delivery to said meter circuit.

6. The ohmmeter of claim 1, further comprising a balance potentiometer for adjusting the combined gain of said input circuit and said meter circuit.

7. The ohmmeter of claim 1, wherein said guard circuit is comprised of a shield cable having an insulating core and a conductive outer layer in electrical communication with said output of said meter circuit.

8. The ohmmeter of claim 1, wherein said probe has a guard electrode spaced from said contact electrodes and connected to said guard circuit, for avoiding shunt resistances.

9. The ohmmeter of claim 8, wherein said electrodes are housed in a probe head and connected to their respective connection nodes by means of a triaxial cable.

10. The ohmmeter of claim 1, wherein said contact electrodes are concentric rings for providing an annular unknown resistance.

11. The ohmmeter of claim 1, wherein said quick charge switch connects said input circuit to said voltage supply circuit during said charging.

12. The ohmmeter of claim 1, wherein said quick charge switch connects said input circuit to said unknown resistance when said charging is not occurring.

* * * * *